United States Patent
Dahme

(10) Patent No.: US 10,444,196 B2
(45) Date of Patent: Oct. 15, 2019

(54) BANDWIDTH-SELECTABLE ACOUSTIC EMISSION APPARATUS AND METHODS FOR TRANSMITTING TIME-AVERAGED SIGNAL DATA

(71) Applicant: Fisher Controls International LLC, Marshalltown, IA (US)

(72) Inventor: Bret Anthony Dahme, Marshalltown, IA (US)

(73) Assignee: FISHER CONTROLS INTERNATIONAL LLC, Marshalltown, IA (US)

(*) Notice: Subject to any disclaimer, the term of this patent is extended or adjusted under 35 U.S.C. 154(b) by 132 days.

(21) Appl. No.: 15/710,270

(22) Filed: Sep. 20, 2017

(65) Prior Publication Data
US 2019/0086366 A1   Mar. 21, 2019

(51) Int. Cl.
*G01N 29/14* (2006.01)
*H04R 3/04* (2006.01)
(Continued)

(52) U.S. Cl.
CPC .......... *G01N 29/14* (2013.01); *G01M 13/003* (2019.01); *G01M 13/028* (2013.01);
(Continued)

(58) Field of Classification Search
CPC ...... G01N 29/14; G01N 29/42; G01N 29/449; G01N 2291/0258; H04R 3/04; G01M 13/003; G01M 13/028; G01M 13/045
(Continued)

(56) References Cited

U.S. PATENT DOCUMENTS

| 4,327,576 A | 5/1982 | Dickey et al. |
| 4,488,240 A * | 12/1984 | Kapadia .................. G07C 3/00 700/74 |

(Continued)

FOREIGN PATENT DOCUMENTS

| EP | 0288979 | 11/1988 |
| EP | 2623949 | 8/2013 |

(Continued)

OTHER PUBLICATIONS

International Searching Authority, "International Search Report," issued in connection with International Patent Application No. PCT/US2018/048121, dated Nov. 20, 2018, 6 pages.
(Continued)

*Primary Examiner* — Lisa M Caputo
*Assistant Examiner* — Rose M Miller
(74) *Attorney, Agent, or Firm* — Hanley, Flight & Zimmerman, LLC

(57) ABSTRACT

Bandwidth-selectable acoustic emission apparatus and methods for transmitting time-averaged signal data are described. An example apparatus includes an acoustic emission sensor having a bandwidth-selectable filter and a data extractor. The acoustic emission sensor is to generate an acoustic emission signal. The bandwidth-selectable filter is to filter the acoustic emission signal based on a selected bandwidth to generate a filtered acoustic emission signal. The data extractor is to extract time-averaged signal data from the filtered acoustic emission signal. The data extractor is also to transmit the time-averaged signal data from the acoustic emission sensor to an external data acquisition system.

20 Claims, 9 Drawing Sheets

(51) Int. Cl.
*G01M 13/003* (2019.01)
*G01M 13/045* (2019.01)
*G01M 13/028* (2019.01)
*G01N 29/42* (2006.01)
*G01N 29/44* (2006.01)

(52) U.S. Cl.
CPC .......... *G01M 13/045* (2013.01); *G01N 29/42* (2013.01); *G01N 29/449* (2013.01); *H04R 3/04* (2013.01); *G01N 2291/0258* (2013.01)

(58) Field of Classification Search
USPC .......................................................... 73/587
See application file for complete search history.

(56) References Cited

U.S. PATENT DOCUMENTS

| | | | |
|---|---|---|---|
| 4,768,380 A * | 9/1988 | Vermeiren | G01H 1/003 340/682 |
| 5,142,916 A | 9/1992 | Yamaguchi | |
| 5,679,900 A | 10/1997 | Smulders | |
| 6,868,348 B1 * | 3/2005 | Stoutenburg | G01M 7/025 702/56 |
| 2005/0204820 A1 * | 9/2005 | Treiber | G01N 29/14 73/649 |
| 2007/0182581 A1 | 8/2007 | Elwell | |
| 2010/0139403 A1 | 6/2010 | Liang et al. | |
| 2014/0182381 A1 | 7/2014 | Comeaux et al. | |
| 2015/0377667 A1 | 12/2015 | Ahmad et al. | |
| 2016/0011072 A1 | 1/2016 | Hale | |
| 2016/0369624 A1 | 12/2016 | Ahmad et al. | |
| 2017/0131240 A1 | 5/2017 | Aura et al. | |
| 2018/0341248 A1 | 11/2018 | Mehr et al. | |
| 2019/0088240 A1 * | 3/2019 | Dahme | G10K 11/02 |

FOREIGN PATENT DOCUMENTS

| | | |
|---|---|---|
| JP | S61182574 | 8/1986 |
| JP | H07120440 | 5/1995 |

OTHER PUBLICATIONS

International Searching Authority, "Written Opinion," issued in connection with International Patent Application No. PCT/US2018/048121, dated Nov. 20, 2018, 9 pages.

International Searching Authority, "International Search Report," issued in connection with International Patent Application No. PCT/US2018/050320, dated Dec. 20, 2018, 6 pages.

ntemational Searching Authority, "Written Opinion," issued in connection with International Patent Application No. PCT/US2018/050320, dated Dec. 20, 2018, 6 pages.

United States Patent and Trademark Office, "Non-Final Office Action," issued in connection with U.S. Appl. No. 15/710,244, dated Apr. 2, 2019, 20 pages.

* cited by examiner

BANDWIDTH-SELECTABLE ACOUSTIC EMISSION APPARATUS AND METHODS FOR TRANSMITTING TIME-AVERAGED SIGNAL DATA

FIELD OF THE DISCLOSURE

This disclosure relates generally to acoustic emission apparatus and methods and, more specifically, to bandwidth-selectable acoustic emission apparatus and methods for transmitting time-averaged signal data.

BACKGROUND

Acoustic emission sensors generate acoustic emission signals (e.g., an electrical voltage signal) in response to acoustic emissions (e.g., transient elastic waves) sensed, measured and/or detected via a sensing element (e.g., one or more piezoelectric crystals) of the acoustic emission sensor. Sources of acoustic emissions may include the formation and/or propagation of a material defect (e.g., a crack), slip and/or dislocation movements of a material, etc.

Conventional acoustic emission measurement and detection environments include an acoustic emission sensor, a preamplifier, a filter, an amplifier, an analog to digital converter, and a data processing device (e.g., a computer). In such conventional environments, the acoustic emission signals are typically conditioned and/or modified via the preamplifier, the filter, the amplifier, and the analog to digital converter, and then subsequently analyzed at the data processing device to detect and/or characterize acoustic emission events (e.g., formation and/or propagation of a material defect, determination of a leakage rate, etc.) associated with the acoustic emission signals.

SUMMARY

Bandwidth-selectable acoustic emission apparatus and methods for transmitting time-averaged signal data are disclosed herein. In some disclosed examples, an apparatus comprises an acoustic emission sensor including a bandwidth-selectable filter and a data extractor. In some disclosed examples, the acoustic emission sensor is to generate an acoustic emission signal. In some disclosed examples, the bandwidth-selectable filter is to filter the acoustic emission signal based on a selected bandwidth to generate a filtered acoustic emission signal. In some disclosed examples, the data extractor is to extract time-averaged signal data from the filtered acoustic emission signal. In some disclosed examples, the data extractor is also to transmit the time-averaged signal data from the acoustic emission sensor to an external data acquisition system.

In some disclosed examples, a method comprises filtering an acoustic emission signal based on a selected bandwidth of a bandwidth-selectable filter of an acoustic emission sensor to generate a filtered acoustic emission signal. In some disclosed examples, the acoustic emission signal is generated via the acoustic emission sensor. In some disclosed examples, the method further comprises extracting time-averaged signal data from the filtered acoustic emission signal. In some disclosed examples, the method further comprises transmitting the time-averaged signal data from the acoustic emission sensor to an external data acquisition system.

In some disclosed examples, an apparatus comprises an external preamplifier device including a bandwidth-selectable filter and a data extractor. In some disclosed examples, the external preamplifier device is to receive an acoustic emission signal from an acoustic emission sensor. In some disclosed examples, the bandwidth-selectable filter is to filter the acoustic emission signal based on a selected bandwidth to generate a filtered acoustic emission signal. In some disclosed examples, the data extractor is to extract time-averaged signal data from the filtered acoustic emission signal. In some disclosed examples, the data extractor is also to transmit the time-averaged signal data from the external preamplifier device to an external data acquisition system.

In some disclosed examples, a method comprises filtering an acoustic emission signal based on a selected bandwidth of a bandwidth-selectable filter of an external preamplifier device to generate a filtered acoustic emission signal. In some disclosed examples, the acoustic emission signal is received at the external preamplifier device from an acoustic emission sensor. In some disclosed examples, the method further comprises extracting time-averaged signal data from the filtered acoustic emission signal. In some disclosed examples, the method further comprises transmitting the time-averaged signal data from the external preamplifier device to an external data acquisition system.

Figure 1:
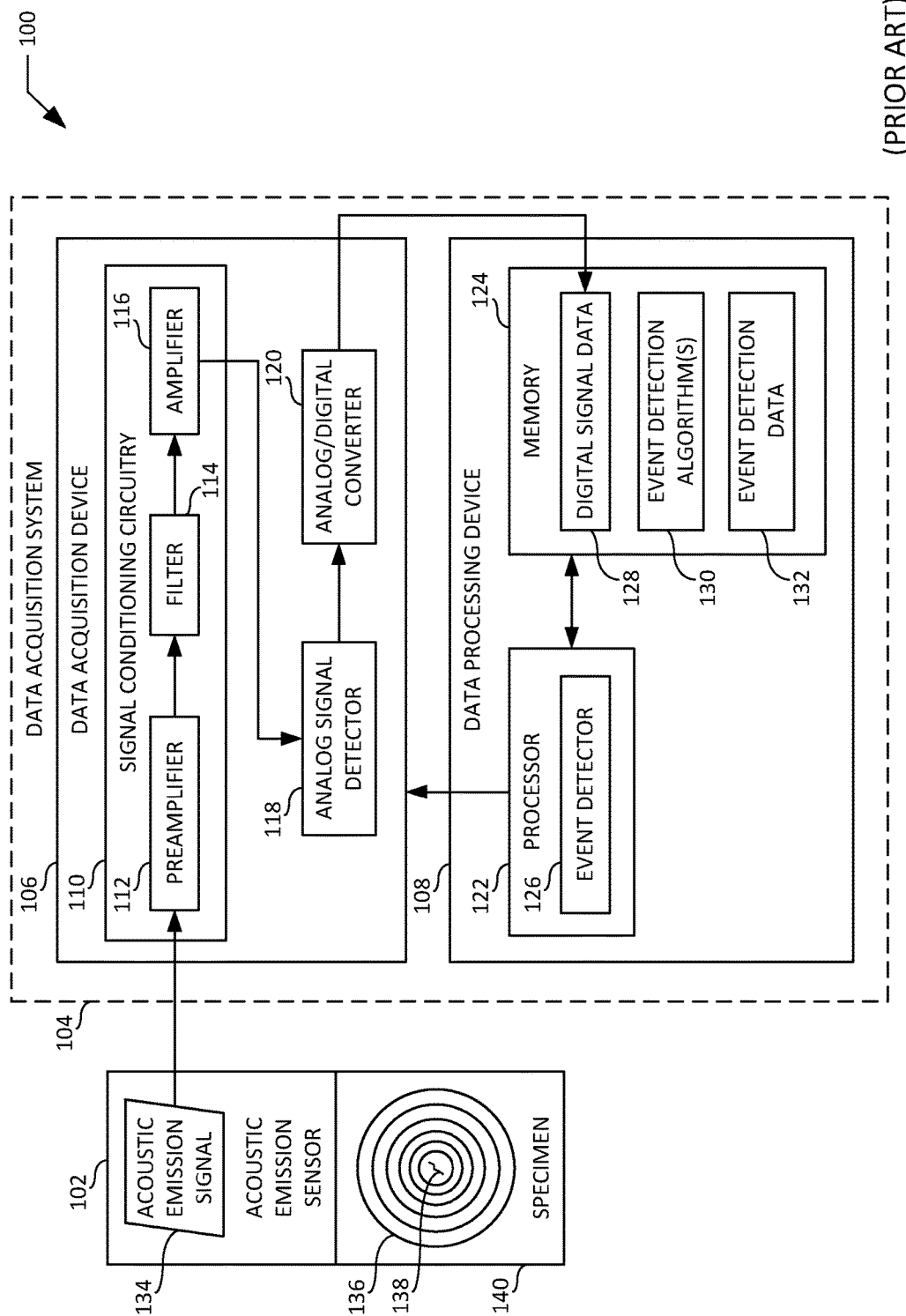
FIG. 1 is a block diagram of a known acoustic emission measurement and detection environment.

Certain examples are shown in the above-identified figures and described in detail below. In describing these examples, like or identical reference numbers are used to identify the same or similar elements. The figures are not necessarily to scale and certain features and certain views of the figures may be shown exaggerated in scale or in schematic for clarity and/or conciseness.

DETAILED DESCRIPTION

Conventional acoustic emission measurement and detection environments include an acoustic emission sensor, a preamplifier, a filter, an amplifier, an analog to digital converter, and a data processing device (e.g., a computer). In such conventional environments, the acoustic emission signals are typically conditioned and/or modified via the preamplifier, the filter, the amplifier, and the analog to digital converter, and then subsequently analyzed at the data processing device to detect and/or characterize acoustic emission events (e.g., formation and/or propagation of a material defect, determination of a leakage rate, etc.) associated with the acoustic emission signals.

In some known acoustic emission measurement and detection environments, signal conditioning circuitry including the preamplifier, the filter, and the amplifier is included within a data acquisition device that also includes the analog to digital converter. In other known acoustic emission measurement and detection environments, the preamplifier and the filter of the signal conditioning circuitry are integrated within the acoustic emission sensor, rather than being integrated within the data acquisition device. In still other known acoustic emission measurement and detection environments, the preamplifier and the filter of the signal conditioning circuitry are integrated within an external preamplifier device operatively located and/or positioned between the acoustic emission sensor and the data acquisition device, rather than being integrated within the data acquisition device.

The above-described conventional acoustic emission measurement and detection environments require high speed sampling (e.g., via the data acquisition device) and extensive post-processing (e.g., via the data processing device) to produce useful information regarding the integrity and/or health of the material(s) (e.g., process equipment) being monitored and/or evaluated. Such high speed sampling and extensive post-processing requirements necessitate the implementation of high end data acquisition and data processing equipment, which increases the complexity and the cost of the acoustic emission measurement and detection system. The implementation of such high end equipment becomes technologically challenging in low power and/or hazardous environments.

Unlike the above-described conventional acoustic emission measurement and detection environments, the acoustic emission apparatus and methods disclosed herein include a bandwidth-selectable filter (e.g., a software-programmable analog filter). In some disclosed examples, the bandwidth-selectable filter is integrated within an acoustic emission sensor. In other examples, the bandwidth-selectable filter is integrated within an external preamplifier device operatively located and/or positioned between an acoustic emission sensor and a data acquisition device.

Implementing the bandwidth-selectable filter via the disclosed bandwidth-selectable acoustic emission apparatus and methods advantageously enables the frequency content of an acoustic emission signal generated by an acoustic emission sensor to be resolved without the need for high speed sampling (e.g., without the need for a high end and costly data acquisition device). For example, an acoustic emission sensor or an external preamplifier device implementing the bandwidth-selectable filter may extract time-averaged signal data (e.g., root mean square (RMS) data, average signal level (ASL) data, etc.) from an acoustic emission signal filtered by the bandwidth-selectable filter, where the bandwidth-selectable filter is programmed and/or configured to filter the acoustic emission signal at one or more desired bandwidth(s)). The extracted time-averaged signal data, which has a lower frequency relative to the frequency of the acoustic emission signal itself, may then be transmitted from the acoustic emission sensor or the external preamplifier device to an external data acquisition device and/or an external data processing device without the need for high speed sampling. Before describing the details of the disclosed bandwidth-selectable acoustic emission apparatus and methods, a description of a known acoustic emission measurement and detection environment is provided in connection with FIG. 1.

FIG. 1 is a block diagram of a known acoustic emission measurement and detection environment 100. The acoustic emission measurement and detection environment 100 of FIG. 1 includes an acoustic emission sensor 102 and a data acquisition system 104. The data acquisition system 104 of FIG. 1 includes a data acquisition device 106 and a data processing device 108 (e.g., a computer). The data acquisition device 106 includes signal conditioning circuitry 110 implemented as a preamplifier 112, a filter 114, and an amplifier 116. The data acquisition device 106 also includes an analog signal detector 118 and an analog to digital converter 120. The data processing device 108 includes a processor 122 and a memory 124. The processor 122 includes and/or implements an event detector 126. The memory 124 stores digital signal data 128, one or more event detection algorithm(s) 130, and event detection data 132. The processor 122 and/or, more generally, the data processing device 108 of FIG. 1 controls the operation of the data acquisition device 106 of FIG. 1

The acoustic emission sensor 102 of FIG. 1 generates an acoustic emission signal 134 in response to one or more acoustic emission(s) (e.g., transient elastic waves 136 of FIG. 1) sensed, measured and/or detected via a sensing element of the acoustic emission sensor 102. The sensing element of the acoustic emission sensor 102 is implemented as one or more piezoelectric crystal(s), as is known in the art. The acoustic emission(s) (e.g., the transient elastic waves 136) are sensed, measured and/or detected by the sensing element of the acoustic emission sensor 102 in response to the formation and/or propagation of a defect (e.g. a crack 138 of FIG. 1) in a specimen 140 of FIG. 1 to which the acoustic emission sensor 102 is coupled. The specimen 140 of FIG. 1 may be an item of process equipment (e.g., a segment of piping and/or conduit, a field device, etc.). The acoustic emission signal 134 generated by the acoustic emission sensor 102 is an analog signal. The generated acoustic emission signal 134 is transmitted to and/or received at the data acquisition system 104 of FIG. 1. More specifically, the acoustic emission signal 134 is transmitted to and/or received at the preamplifier 112 of the signal conditioning circuitry 110 of the data acquisition device 106 of the data acquisition system 104 of FIG. 1.

The signal conditioning circuitry 110 of the data acquisition device 106 of FIG. 1 conditions, alters and/or otherwise prepares the generated acoustic emission signal 134 for further processing. The preamplifier 112 of the signal conditioning circuitry 110 of FIG. 1 amplifies, boosts and/or strengthens the generated acoustic emission signal 134. The amplified acoustic emission signal is transmitted from the preamplifier 112 to the filter 114 of the signal conditioning circuitry 110 of FIG. 1. The filter 114 filters the amplified acoustic emission signal based on a non-selectable and/or non-programmable bandwidth associated with the filter 114. The filtered acoustic emission signal is transmitted from the filter 114 to the amplifier 116 of the signal conditioning circuitry 110 of FIG. 1. The amplifier 116 further amplifies, boosts and/or strengthens the filtered acoustic emission signal. The amplified acoustic emission signal is transmitted from the amplifier 116 to the analog signal detector 118 of the data acquisition device 106 of FIG. 1.

Figure 2:
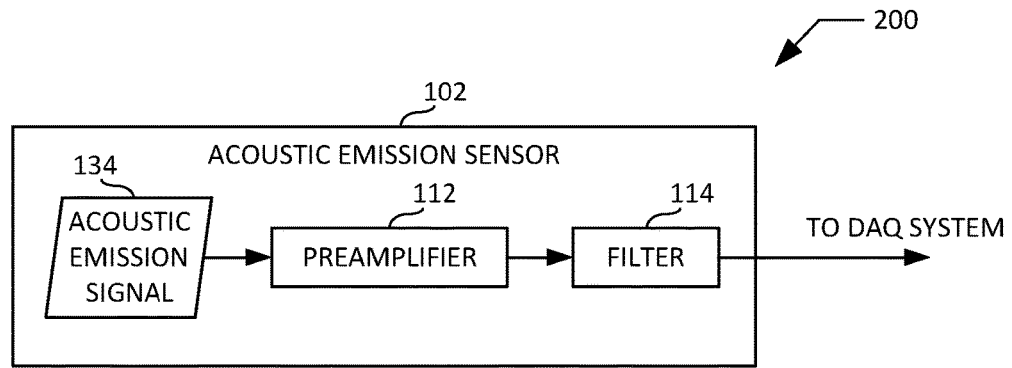
FIG. 2 is a block diagram of a known implementation of the acoustic emission sensor of FIG. 1 modified to include the preamplifier and the filter of FIG. 1.
Figure 3:
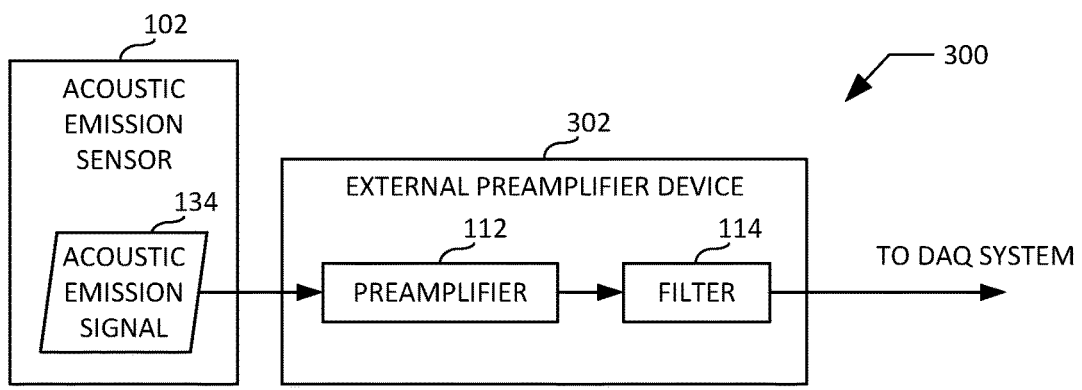
FIG. 3 is a block diagram of a known implementation of an external preamplifier device operatively coupled to the acoustic emission sensor of FIG. 1.

In some known alternative implementations, the preamplifier 112, the filter 114, and/or the amplifier 116 of the signal conditioning circuitry 110 is/are located at (e.g., integrated within) the acoustic emission sensor 102 of FIG. 1, and/or at an external preamplifier device operatively located and/or positioned between the acoustic emission sensor 102 of FIG. 1 and the data acquisition system 104 of FIG. 1. For example, FIG. 2 is a block diagram of a known implementation 200 of the acoustic emission sensor 102 of FIG. 1 modified to include the preamplifier 112 and the filter 114 of FIG. 1. In the example of FIG. 2, the above-described operations and/or functions of the preamplifier 112 and the filter 114 of FIG. 1 are performed at the acoustic emission sensor 102 of FIG. 2, as opposed to being performed at the data acquisition device 106 of the data acquisition system 104 of FIG. 1. As another example, FIG. 3 is a block diagram of a known implementation 300 of an external preamplifier device 302 operatively located and/or positioned between the acoustic emission sensor 102 of FIG. 1 and the data acquisition system 104 of FIG. 1. In the example of FIG. 3, the above-described operations and/or functions of the preamplifier 112 and the filter 114 of FIG. 1 are performed at the external preamplifier device 302 of FIG. 3, as opposed to being performed at the data acquisition device 106 of the data acquisition system 104 of FIG. 1.

Returning to the known acoustic emission measurement and detection environment 100 of FIG. 1, the analog signal detector 118 of the data acquisition device 106 detects the amplified signal transmitted from the amplifier 116 of the signal conditioning circuitry 110 as an analog waveform. The analog to digital converter 120 of the data acquisition device 106 converts the detected analog waveform into the digital signal data 128. The digital signal data 128 is transmitted from the analog to digital converter 120 to the memory 124 of the data processing device 108 of FIG. 1 where the digital signal data 128 is stored for further processing via the processor 122 of the data processing device 108 of FIG. 1.

The processor 122 of the data processing device 108 of FIG. 1 implements the event detector 126 to detect the formation and/or propagation of one or more defect(s) (e.g., the crack 138 of FIG. 1) in the specimen 140 of FIG. 1. The event detector 126 detects one or more event(s) associated with the defect(s) (e.g., a leakage rate associated with the formation and/or propagation of the defect) based on the one or more event detection algorithm(s) 130 stored in the memory 124 and accessible to the processor 122 and/or the event detector 126. The event detector 126 and/or, more generally, the processor 122 of the data processing device 108 of FIG. 1 transmits the event detection data 132 (e.g., data corresponding to one or more event(s) detected by the event detector 126) to the memory 124 of the data processing device 108 where the event detection data 132 is stored for further analysis and/or processing by the processor 122.

Figure 4:
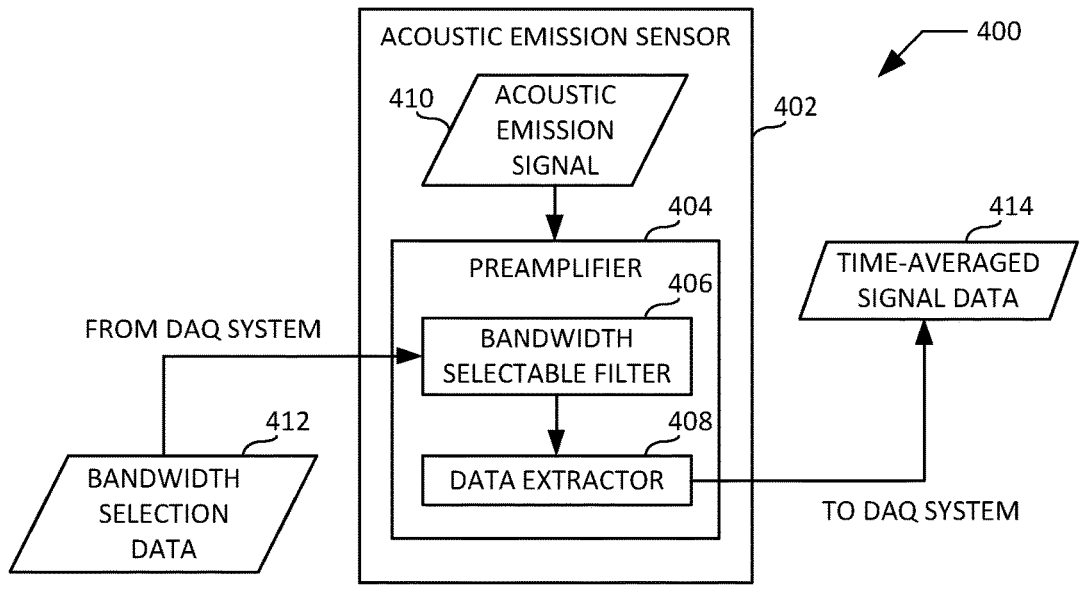
FIG. 4 is a block diagram of an example acoustic emission sensor including an example preamplifier, and example bandwidth-selectable filter, and an example data extractor arranged in a first example configuration in accordance with the teachings of this disclosure.

FIG. 4 is a block diagram of an example acoustic emission sensor 402 including an example preamplifier 404, an example bandwidth-selectable filter 406, and an example data extractor 408 arranged in a first example configuration 400 in accordance with the teachings of this disclosure. In the first configuration 400 of FIG. 4, the bandwidth-selectable filter 406 and the data extractor 408 are integrated within the preamplifier 404 of the acoustic emission sensor 402. In some examples, the acoustic emission sensor 402 of FIG. 4 may include a case (not shown) that houses and/or contains the preamplifier 404, the bandwidth-selectable filter 406, and the data extractor 408 of FIG. 4.

The acoustic emission sensor 402 of FIG. 4 generates an example acoustic emission signal 410 in response to one or more acoustic emission(s) (e.g., transient elastic waves) sensed, measured and/or detected via a sensing element of the acoustic emission sensor 402. In some examples, the sensing element of the acoustic emission sensor 402 may be implemented as one or more piezoelectric crystal(s), as is known in the art. In some examples, the acoustic emission signal 410 generated by the acoustic emission sensor 402 is an analog signal. The acoustic emission signal 410 generated by the acoustic emission sensor 402 of FIG. 4 is transmitted to and/or received at the preamplifier 404 of the acoustic emission sensor 402 of FIG. 4.

The preamplifier 404 of FIG. 4 amplifies, boosts and/or strengthens the acoustic emission signal 410 generated by the acoustic emission sensor 402. In the illustrated example of FIG. 4, the preamplifier 404 amplifies, boosts and/or strengthens the acoustic emission signal 410 prior to the acoustic emission signal 410 being transmitted to and/or received at the bandwidth-selectable filter 406 of the acoustic emission sensor 402 of FIG. 4. In other examples, the preamplifier 404 of FIG. 4 may amplify, boost and/or strengthen the acoustic emission signal 410 after the acoustic emission signal 410 is filtered by the bandwidth-selectable filter 406 of the acoustic emission sensor 402 of FIG. 4.

The bandwidth-selectable filter 406 of FIG. 4 filters the acoustic emission signal 410 (e.g., the acoustic emission signal as amplified by the preamplifier 404 of FIG. 4) based on a selected bandwidth to generate a filtered acoustic emission signal. In some examples, the bandwidth-selectable filter 406 may be implemented as a programmable and/or configurable analog filter. The bandwidth-selectable filter 406 may be any type of filter including, for example, active, passive, superheterodyne, envelope detection, capacitor switching, field programmable gate array, finite impulse response, infinite impulse response, etc. The filtered acoustic emission signal generated by the bandwidth-selectable filter 406 of FIG. 4 is transmitted to and/or received at the data extractor 408 of the acoustic emission sensor 402 of FIG. 4.

In the illustrated example of FIG. 4, the selected bandwidth of the bandwidth-selectable filter 406 is based on example bandwidth selection data 412 transmitted to and/or received at the bandwidth-selectable filter 406 from an external data acquisition system. The selected bandwidth indicated by and/or corresponding to the bandwidth selection data 412 may include a single bandwidth or a range of bandwidths at which the bandwidth-selectable filter 406 is to filter the acoustic emission signal 410. Thus, the bandwidth-selectable filter 406 is configured (e.g., via the bandwidth-selectable filter 406 itself and/or, more generally, via the acoustic emission sensor 402) to operate and/or function (e.g., to filter) at the selected bandwidth(s) indicated by and/or corresponding to the bandwidth selection data 412 of FIG. 4. In some examples, the bandwidth selection data 412 may be communicated to the bandwidth-selectable filter 406 over a network via a Highway Addressable Remote Transducer (HART) communication protocol. In some examples, the external data acquisition system may include a data acquisition device and/or a data processing device.

The data extractor 408 of FIG. 4 extracts example time-averaged signal data 414 (e.g., root mean square (RMS) data, average signal level (ASL) data, etc.), from the filtered acoustic emission signal generated by the bandwidth-selectable filter 406 of FIG. 4. For example, the data extractor 408 may extract and/or calculate root mean square data (e.g., a form of the time-averaged signal data 414) from the filtered acoustic emission signal by squaring the values of the filtered acoustic emission signal (e.g., squaring the function that defines the waveform of the filtered acoustic emission signal), by taking the average of the squared values (e.g., the average of the squared function), and by taking the square root of the average values (e.g., the square root of the average function). As another example, the data extractor 408 may additionally or alternatively extract and/or calculate average signal level data (e.g., another form of the time-averaged signal data 414) from the filtered acoustic emission signal by taking the average signal values (e.g., the average of the function that defines the waveform of the filtered acoustic emission signal) as a function of time.

In the illustrated example of FIG. 4, the data extractor 408 also transmits the time-averaged signal data 414 from the acoustic emission sensor 402 of FIG. 4 to an external data acquisition system. Thus, the data extractor 408 and/or, more generally, the acoustic emission sensor 402, transmits the time-averaged signal data 414 as filtered by the bandwidth-selectable filter 406 of the acoustic emission sensor 402 based on the selected bandwidth(s) corresponding to the bandwidth selection data 412 of FIG. 4. In some examples, the time-averaged signal data 414 may be the only data transmitted to the external data acquisition system by the data extractor 408 and/or the acoustic emission sensor 402. In some examples, the time-averaged signal data 414 may be communicated to the external data acquisition system over a network via a HART communication protocol. In other examples, the time-averaged signal data 414 may be communicated to the external data acquisition system over a network via analog communication (e.g., 4-20 milliamp wiring). In some examples, the external data acquisition system may include a data acquisition device and/or a data processing device.

Figure 5:
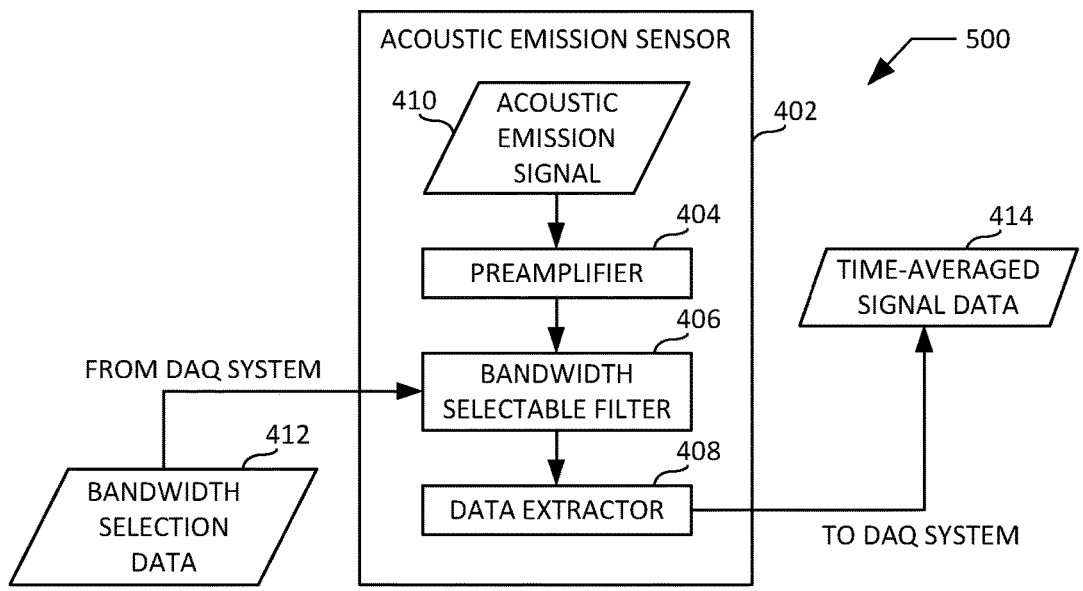
FIG. 5 is a block diagram of the example acoustic emission sensor of FIG. 4 including the example preamplifier, the example bandwidth-selectable filter, and the example data extractor of FIG. 4 arranged in a second example configuration in accordance with the teachings of this disclosure.

FIG. 5 is a block diagram of the example acoustic emission sensor 402 of FIG. 4 including the example preamplifier 404, the example bandwidth-selectable filter 406, and the example data extractor 408 arranged in a second example configuration 500 in accordance with the teachings of this disclosure. Unlike the first configuration 400 of FIG. 4 which shows the bandwidth-selectable filter 406 of FIG. 4 and the data extractor 408 of FIG. 4 integrated within the preamplifier 404 of FIG. 4, the second configuration 500 of FIG. 5 shows the bandwidth-selectable filter 406 and the data extractor 408 as not being integrated within the preamplifier 404 of FIG. 5. The structure, function and/or operation of the acoustic emission sensor 402, the preamplifier 404, the bandwidth-selectable filter 406, and the data extractor 408 as shown in the second configuration 500 of FIG. 5 are otherwise similar to the structure, function and/or operation of the acoustic emission sensor 402, the preamplifier 404, the bandwidth-selectable filter 406, and the data extractor 408 as shown in the first configuration 400 of FIG. 4 described above.

Figure 6:
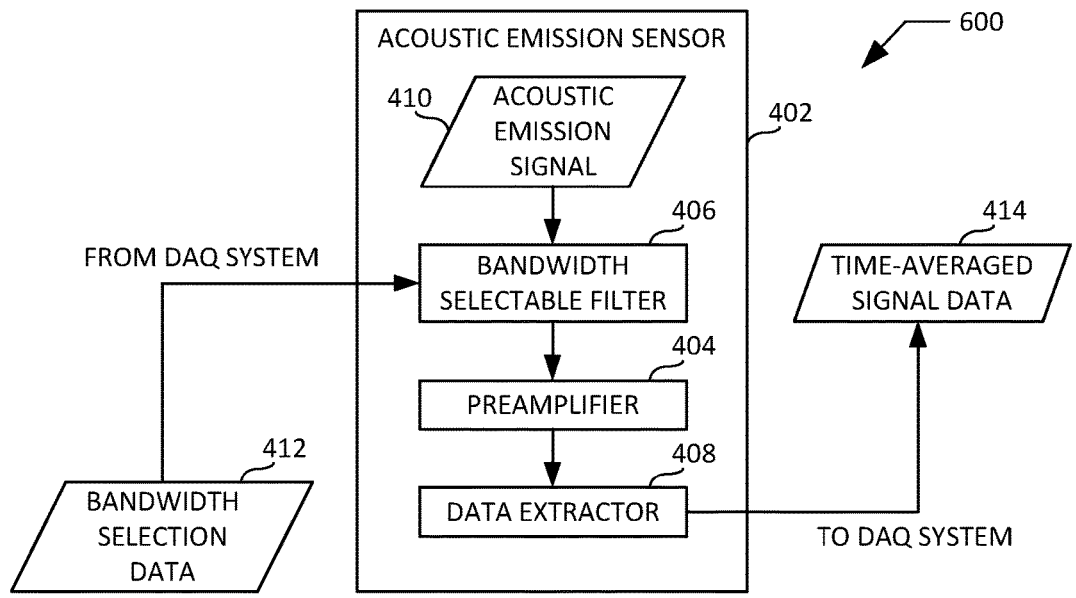
FIG. 6 is a block diagram of the example acoustic emission sensor of FIGS. 4 and 5 including the example preamplifier, the example bandwidth-selectable filter, and the example data extractor of FIGS. 4 and 5 arranged in a third example configuration in accordance with the teachings of this disclosure.

FIG. 6 is a block diagram of the example acoustic emission sensor 402 of FIGS. 4 and 5 including the example preamplifier 404, the example bandwidth-selectable filter 406, and the example data extractor 408 arranged in a third example configuration 600 in accordance with the teachings of this disclosure. In the third configuration 600 of FIG. 6, the preamplifier 404, the bandwidth-selectable filter 406, and the data extractor 408 are integrated within the acoustic emission sensor 402. Unlike the second configuration 500 of FIG. 5 which shows the bandwidth-selectable filter 406 of FIG. 5 operatively located and/or positioned after the preamplifier 404 of FIG. 5, the third configuration 600 of FIG. 6 shows the bandwidth-selectable filter 406 of FIG. 6 operatively located and/or positioned prior to the preamplifier 404 of FIG. 6.

Thus, in the illustrated example of FIG. 6, the bandwidth-selectable filter 406 of FIG. 6 filters the acoustic emission signal 410 generated by the acoustic emission sensor 402 of FIG. 6 based on the selected bandwidth(s) corresponding to the bandwidth selection data 412 to generate a filtered acoustic emission signal. The filtered acoustic emission signal is thereafter transmitted to and/or received at the preamplifier 404 of FIG. 6, where the filtered acoustic emission signal is amplified and subsequently transmitted to the data extractor 408 of FIG. 6. The structure, function and/or operation of the acoustic emission sensor 402, the preamplifier 404, the bandwidth-selectable filter 406, and the data extractor 408 as shown in the third configuration 600 of FIG. 6 are otherwise similar to the structure, function and/or operation of the acoustic emission sensor 402, the preamplifier 404, the bandwidth-selectable filter 406, and the data extractor 408 as shown in the first configuration 400 of FIG. 4 and/or the second configuration 500 of FIG. 5 described above.

While example manners of implementing the acoustic emission sensor 402 are illustrated in FIGS. 4-6, one or more of the elements, processes and/or devices illustrated in FIGS. 4-6 may be combined, divided, re-arranged, omitted, eliminated and/or implemented in any other way. Further, the example preamplifier 404, the example bandwidth-selectable filter 406, the example data extractor 408 and/or, more generally, the example acoustic emission sensor 402 of FIGS. 4-6 may be implemented by hardware, software, firmware and/or any combination of hardware, software and/or firmware. Thus, for example, any of the example preamplifier 404, the example bandwidth-selectable filter 406, the example data extractor 408 and/or, more generally, the example acoustic emission sensor 402 of FIGS. 4-6 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example preamplifier 404, the example bandwidth-selectable filter 406, the example data extractor 408 and/or, more generally, the example acoustic emission sensor 402 of FIGS. 4-6 is/are hereby expressly defined to include a non-transitory computer readable storage device or storage disk such as a memory, a digital versatile disk (DVD), a compact disk (CD), a Blu-ray disk, etc. including the software and/or firmware. Further still, the example acoustic emission sensor 402 of FIGS. 4-6 may include one or more elements, processes and/or devices in addition to, or instead of, those illustrated in FIGS. 4-6, and/or may include more than one of any or all of the illustrated elements, processes and devices.

Figure 7:
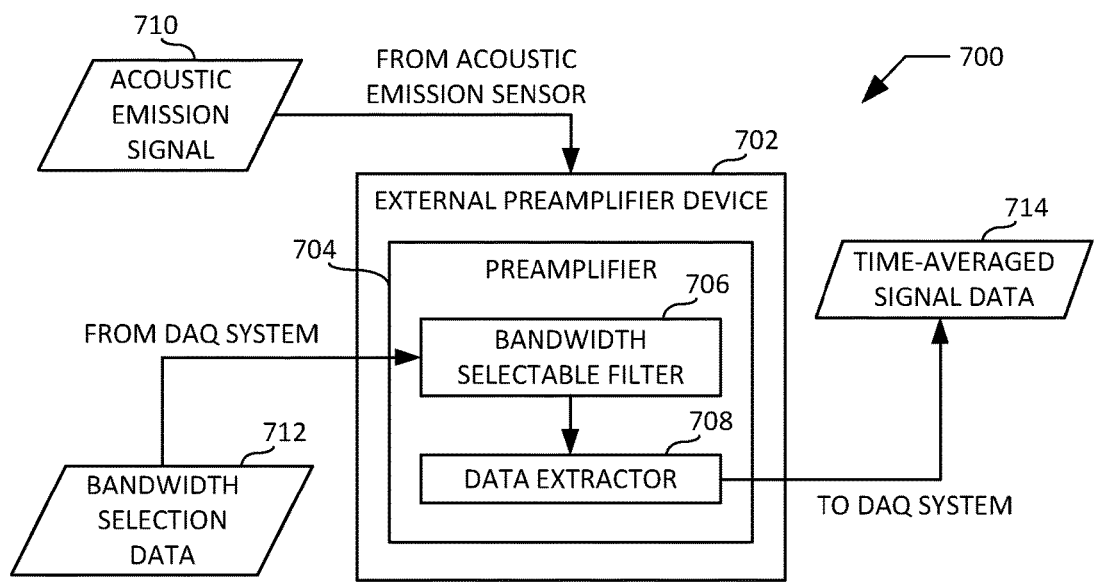
FIG. 7 is a block diagram of an example external preamplifier device including an example preamplifier, an example bandwidth-selectable filter, and an example data extractor arranged in a first example configuration in accordance with the teachings of this disclosure.

FIG. 7 is a block diagram of an example external preamplifier device 702 including an example preamplifier 704, an example bandwidth-selectable filter 706, and an example data extractor 708 arranged in a first example configuration 700 in accordance with the teachings of this disclosure. In the first configuration 700 of FIG. 7, the bandwidth-selectable filter 706 and the data extractor 708 are integrated within the preamplifier 704 of the external preamplifier device 702. In some examples, the external preamplifier device 702 of FIG. 7 may include a case (not shown) that houses and/or contains the preamplifier 704, the bandwidth-selectable filter 706, and the data extractor 708 of FIG. 7.

In the illustrated example of FIG. 7, the external preamplifier device 702 receives an example acoustic emission signal 710 generated by an acoustic emission sensor (not shown). In some examples, the acoustic emission signal 710 received at the external preamplifier device 702 is an analog signal. The acoustic emission signal 710 received at the external preamplifier device 702 of FIG. 7 is transmitted to and/or received at the preamplifier 704 of the external preamplifier device 702 of FIG. 7.

The preamplifier 704 of FIG. 7 amplifies, boosts and/or strengthens the acoustic emission signal 710 received at the external preamplifier device 702. In the illustrated example of FIG. 7, the preamplifier 704 amplifies, boosts and/or strengthens the acoustic emission signal 710 prior to the acoustic emission signal 710 being transmitted to and/or received at the bandwidth-selectable filter 706 of the external preamplifier device 702 of FIG. 7. In other examples, the preamplifier 704 of FIG. 7 may amplify, boost and/or strengthen the acoustic emission signal 710 after the acoustic emission signal 710 is filtered by the bandwidth-selectable filter 706 of the external preamplifier device 702 of FIG. 7.

The bandwidth-selectable filter 706 of FIG. 7 filters the acoustic emission signal 710 (e.g., the acoustic emission signal as amplified by the preamplifier 704 of FIG. 7) based on a selected bandwidth to generate a filtered acoustic emission signal. In some examples, the bandwidth-selectable filter 706 may be implemented as a programmable and/or configurable analog filter. The bandwidth-selectable filter 706 may be any type of filter including, for example, active, passive, superheterodyne, envelope detection, capacitor switching, field programmable gate array, finite impulse response, infinite impulse response, etc. The filtered acoustic emission signal generated by the bandwidth-selectable filter 706 of FIG. 7 is transmitted to and/or received at the data extractor 708 of the external preamplifier device 702 of FIG. 7.

In the illustrated example of FIG. 7, the selected bandwidth of the bandwidth-selectable filter 706 is based on example bandwidth selection data 712 transmitted to and/or received at the bandwidth-selectable filter 706 from an external data acquisition system. The selected bandwidth indicated by and/or corresponding to the bandwidth selection data 712 may include a single bandwidth or a range of bandwidths at which the bandwidth-selectable filter 706 is to filter the acoustic emission signal 710. Thus, the bandwidth-selectable filter 706 is configured (e.g., via the bandwidth-selectable filter 706 itself and/or, more generally, via the external preamplifier device 702) to operate and/or function (e.g., to filter) at the selected bandwidth(s) indicated by and/or corresponding to the bandwidth selection data 412 of FIG. 7. In some examples, the bandwidth selection data 712 may be communicated to the bandwidth-selectable filter 706 over a network via a HART communication protocol. In some examples, the external data acquisition system may include a data acquisition device and/or a data processing device.

The data extractor 708 of FIG. 7 extracts example time-averaged signal data 714 (e.g., root mean square (RMS) data, average signal level (ASL) data, etc.) from the filtered acoustic emission signal generated by the bandwidth-selectable filter 706 of FIG. 7. For example, the data extractor 708 may extract and/or calculate root mean square data (e.g., a form of the time-averaged signal data 714) from the filtered acoustic emission signal by squaring the values of the filtered acoustic emission signal (e.g., squaring the function that defines the waveform of the filtered acoustic emission signal), by taking the average of the squared values (e.g., the average of the squared function), and by taking the square root of the average values (e.g., the square root of the average function). As another example, the data extractor 708 may additionally or alternatively extract and/or calculate average signal level data (e.g., another form of the time-averaged signal data 714) from the filtered acoustic emission signal by taking the average signal values (e.g., the average of the function that defines the waveform of the filtered acoustic emission signal) as a function of time.

In the illustrated example of FIG. 7, the data extractor 708 also transmits the time-averaged signal data 714 from the external preamplifier device 702 of FIG. 7 to an external data acquisition system. Thus, the data extractor 708 and/or, more generally, the external preamplifier device 702, transmits the time-averaged signal data 714 as filtered by the bandwidth-selectable filter 706 of the external preamplifier device 702 based on the selected bandwidth(s) corresponding to the bandwidth selection data 712 of FIG. 7. In some examples, the time-averaged signal data 714 may be the only data transmitted to the external data acquisition system by the data extractor 708 and/or the external preamplifier device 702. In some examples, the time-averaged signal data 714 may be communicated to the external data acquisition system over a network via a HART communication protocol. In other examples, the time-averaged signal data 714 may be communicated to the external data acquisition system over a network via analog communication (e.g., 4-20 milliamp wiring). In some examples, the external data acquisition system may include a data acquisition device and/or a data processing device.

Figure 8:
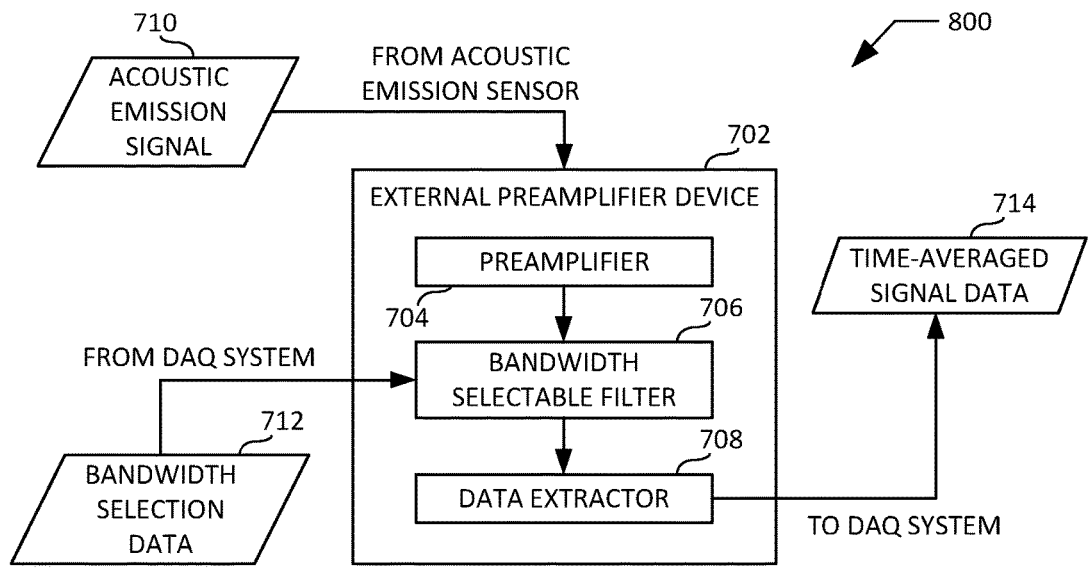
FIG. 8 is a block diagram of the example external preamplifier device of FIG. 7 including the example preamplifier, the example bandwidth-selectable filter, and the example data extractor of FIG. 7 arranged in a second example configuration in accordance with the teachings of this disclosure.

FIG. 8 is a block diagram of the example external preamplifier device 702 of FIG. 7 including the example preamplifier 704, the example bandwidth-selectable filter 706, and the example data extractor 708 of FIG. 7 arranged in a second example configuration 800 in accordance with the teachings of this disclosure. Unlike the first configuration 700 of FIG. 7 which shows the bandwidth-selectable filter 706 of FIG. 7 and the data extractor 708 of FIG. 7 integrated within the preamplifier 704 of FIG. 7, the second configuration 800 of FIG. 8 shows the bandwidth-selectable filter 706 and the data extractor 708 as not being integrated within the preamplifier 704 of FIG. 8. The structure, function and/or operation of the external preamplifier device 702, the preamplifier 704, the bandwidth-selectable filter 706, and the data extractor 708 as shown in the second configuration 800 of FIG. 8 are otherwise similar to the structure, function and/or operation of the external preamplifier device 702, the preamplifier 704, the bandwidth-selectable filter 706, and the data extractor 708 as shown in the first configuration 700 of FIG. 7 described above.

Figure 9:
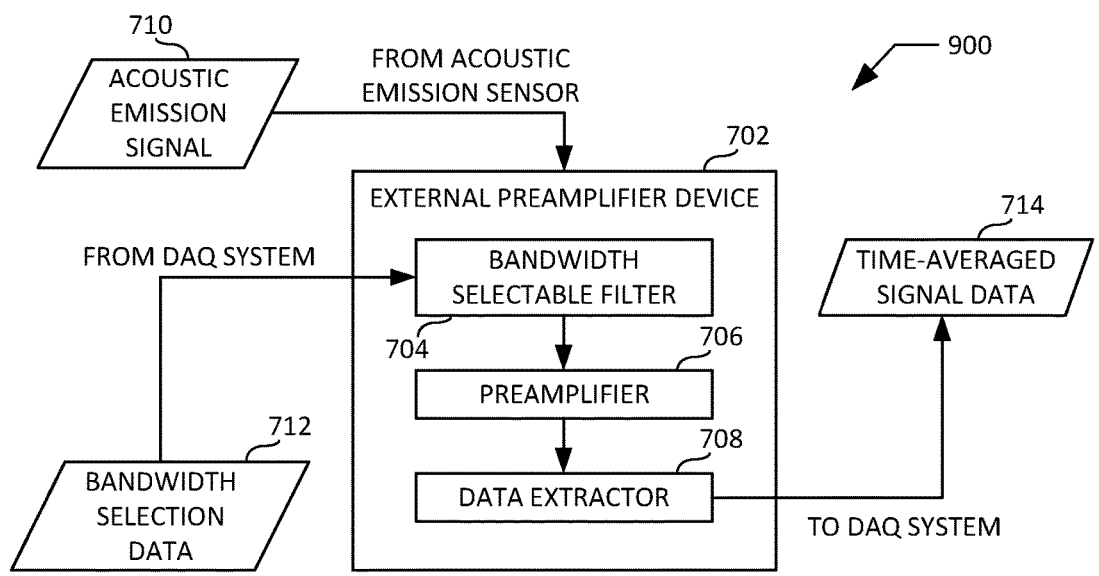
FIG. 9 is a block diagram of the example external preamplifier device of FIGS. 7 and 8 including the example preamplifier, the example bandwidth-selectable filter, and the example data extractor of FIGS. 7 and 8 arranged in a third example configuration in accordance with the teachings of this disclosure.

FIG. 9 is a block diagram of the example external preamplifier device 702 of FIGS. 7 and 8 including the example preamplifier 704, the example bandwidth-selectable filter 706, and the example data extractor 708 of FIGS. 7 and 8 arranged in a third example configuration 900 in accordance with the teachings of this disclosure. In the third configuration 900 of FIG. 9, the preamplifier 704, the bandwidth-selectable filter 706, and the data extractor 708 are integrated within the external preamplifier device 702. Unlike the second configuration 800 of FIG. 8 which shows the bandwidth-selectable filter 706 of FIG. 8 operatively located and/or positioned after the preamplifier 704 of FIG. 8, the third configuration 900 of FIG. 9 shows the bandwidth-selectable filter 706 of FIG. 9 operatively located and/or positioned prior to the preamplifier 704 of FIG. 9.

Thus, in the illustrated example of FIG. 9, the bandwidth-selectable filter 706 of FIG. 9 filters the acoustic emission signal 710 received at the external preamplifier device 702 of FIG. 9 based on the selected bandwidth(s) corresponding to the bandwidth selection data 712 to generate a filtered acoustic emission signal. The filtered acoustic emission signal is thereafter transmitted to and/or received at the preamplifier 704 of FIG. 9, where the filtered acoustic emission signal is amplified and subsequently transmitted to the data extractor 708 of FIG. 9. The structure, function and/or operation of the external preamplifier device 702, the preamplifier 704, the bandwidth-selectable filter 706, and the data extractor 708 as shown in the third configuration 900 of FIG. 9 are otherwise similar to the structure, function and/or operation of the external preamplifier device 702, the preamplifier 704, the bandwidth-selectable filter 706, and the data extractor 708 as shown in the first configuration 700 of FIG. 7 and/or the second configuration 800 of FIG. 8 described above.

While example manners of implementing the external preamplifier device 702 are illustrated in FIGS. 7-9, one or more of the elements, processes and/or devices illustrated in FIGS. 7-9 may be combined, divided, re-arranged, omitted, eliminated and/or implemented in any other way. Further, the example preamplifier 704, the example bandwidth-selectable filter 706, the example data extractor 708 and/or, more generally, the example external preamplifier device 702 of FIGS. 7-9 may be implemented by hardware, software, firmware and/or any combination of hardware, software and/or firmware. Thus, for example, any of the example preamplifier 704, the example bandwidth-selectable filter 706, the example data extractor 708 and/or, more generally, the example external preamplifier device 702 of FIGS. 7-9 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example preamplifier 704, the example bandwidth-selectable filter 706, the example data extractor 708 and/or, more generally, the example external preamplifier device 702 of FIGS. 7-9 is/are hereby expressly defined to include a non-transitory computer readable storage device or storage disk such as a memory, a digital versatile disk (DVD), a compact disk (CD), a Blu-ray disk, etc. including the software and/or firmware. Further still, the example external preamplifier device 702 of FIGS. 7-9 may include one or more elements, processes and/or devices in addition to, or instead of, those illustrated in FIGS. 7-9, and/or may include more than one of any or all of the illustrated elements, processes and devices.

Figure 10:
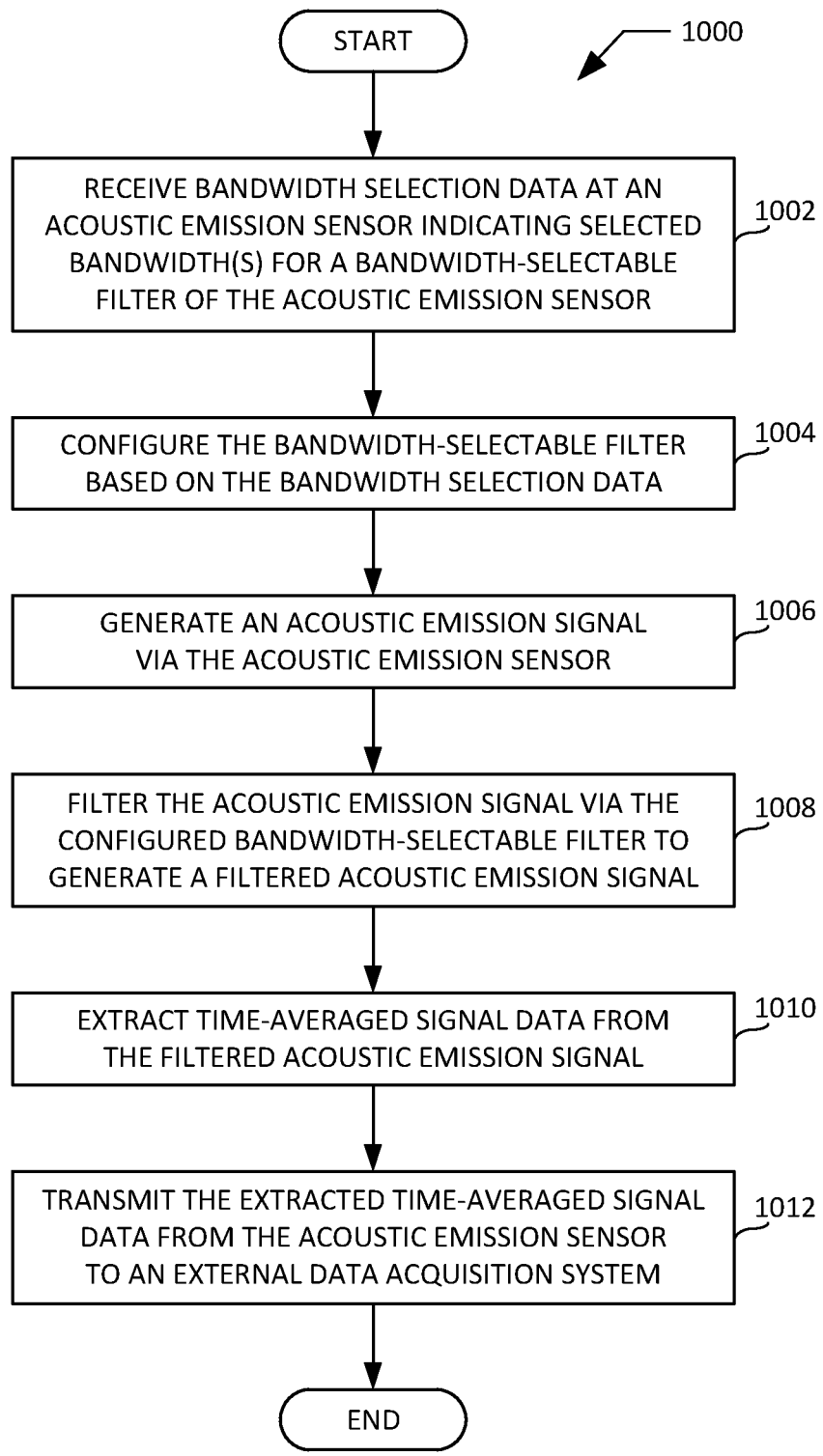
FIG. 10 is a flowchart representative of an example method for transmitting time-averaged signal data from the example acoustic emission sensor of FIGS. 4-6.
Figure 11:
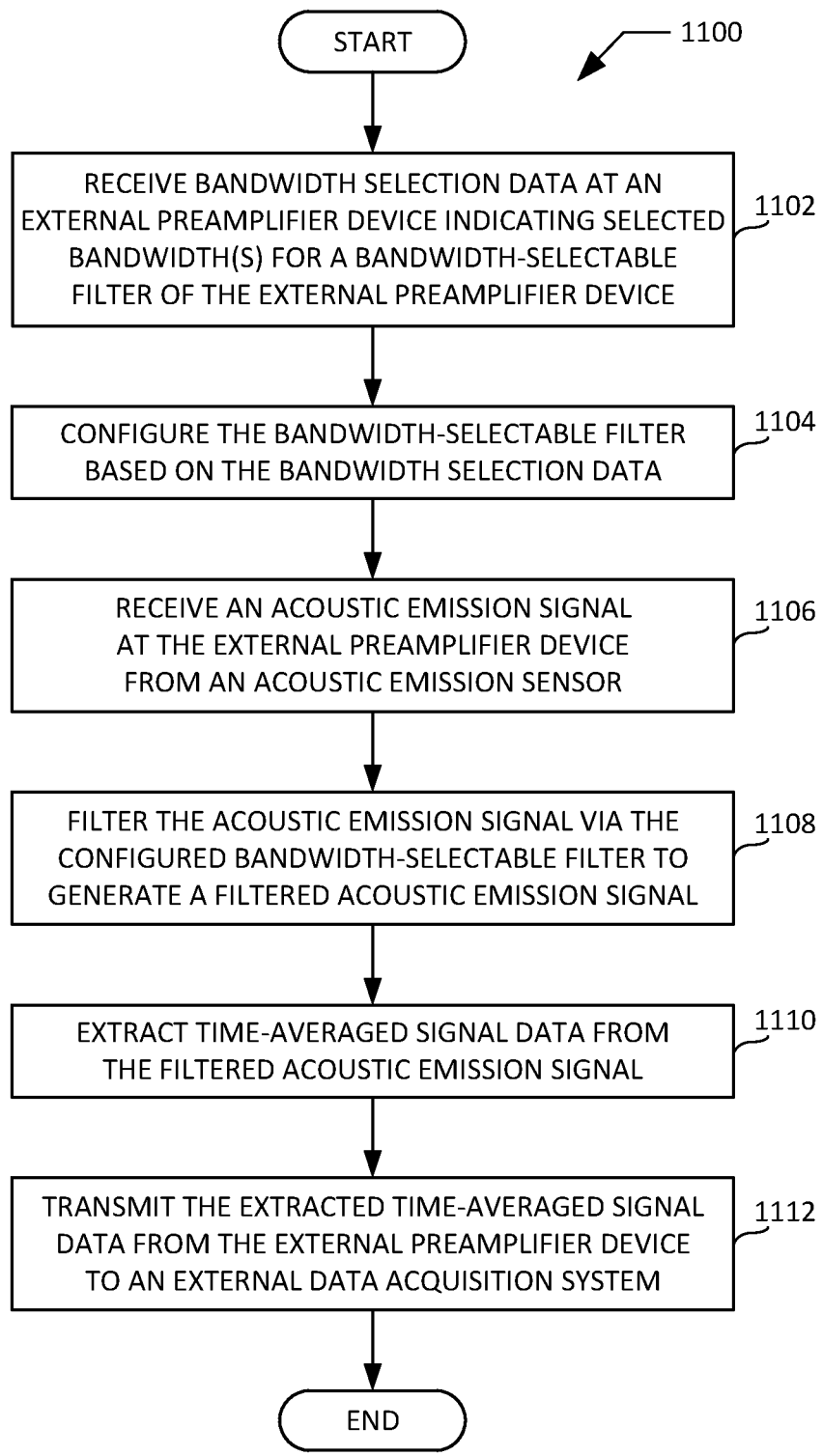
FIG. 11 is a flowchart representative of an example method for transmitting time-averaged signal from the example external preamplifier device of FIGS. 7-9.

Flowcharts representative of example methods for transmitting time-averaged signal data via the example acoustic emission sensor 402 of FIGS. 4-6 and the example external preamplifier device 702 of FIGS. 7-9 are respectively shown in FIGS. 10 and 11. In these examples, the methods may be implemented using machine readable instructions that comprise one or more program(s) for execution by one or more processor(s) such as the processor 1202 shown in the example processor platform 1200 discussed below in connection with FIG. 12, or the processor 1302 shown in the example processor platform 1300 discussed below in connection with FIG. 13. The one or more program(s) may be embodied in software stored on a non-transitory computer readable storage medium such as a CD-ROM, a floppy disk, a hard drive, a digital versatile disk (DVD), a Blu-ray disk, or a memory associated with the processor 1202 or the processor 1302, but the entirety of any program and/or parts thereof could alternatively be executed by a device other than the processor 1202 or the processor 1302, and/or embodied in firmware or dedicated hardware. Further, although the example program(s) is/are described with reference to the flowcharts illustrated in FIGS. 10 and 11, many other methods of implementing the example acoustic emission sensor 402 of FIGS. 4-6 and/or the external preamplifier device 702 of FIGS. 7-9 may alternatively be used. For example, the order of execution of the blocks may be changed, and/or some of the blocks described may be changed, eliminated, or combined. Additionally or alternatively, any or all of the blocks may be implemented by one or more hardware circuits (e.g., discrete and/or integrated analog and/or digital circuitry, a Field Programmable Gate Array (FPGA), an Application Specific Integrated circuit (ASIC), a comparator, an operational-amplifier (op-amp), a logic circuit, etc.) structured to perform the corresponding operation without executing software or firmware.

As mentioned above, the example methods of FIGS. 10 and 11 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. "Including" and "comprising" (and all forms and tenses thereof) are used herein to be open ended terms. Thus, whenever a claim lists anything following any form of "include" or "comprise" (e.g., comprises, includes, comprising, including, etc.), it is to be understood that additional elements, terms, etc. may be present without falling outside the scope of the corresponding claim. As used herein, when the phrase "at least" is used as the transition term in a preamble of a claim, it is open-ended in the same manner as the term "comprising" and "including" are open ended.

FIG. 10 is a flowchart representative of an example method 1000 for transmitting time-averaged signal data from the example acoustic emission sensor 402 of FIGS. 4-6. The example method 1000 of FIG. 10 begins with and/or otherwise includes receiving bandwidth selection data at the acoustic emission sensor indicating one or more selected bandwidth(s) for a bandwidth-selectable filter of the acoustic emission sensor (block 1002). For example, the bandwidth-selectable filter 406 and/or, more generally, the acoustic emission sensor 402 of FIG. 4 may receive the bandwidth selection data 412 of FIG. 4 indicating and/or corresponding to one or more selected bandwidth(s) for the bandwidth-selectable filter 406 of the acoustic emission sensor 402. In some examples, the bandwidth selection data may be received from an external data acquisition system. Following block 1002, control of the example method 1000 of FIG. 10 proceeds to block 1004.

At block 1004, the bandwidth-selectable filter is configured based on the bandwidth selection data (block 1004). For example, the bandwidth-selectable filter 406 and/or, more generally, the acoustic emission sensor 402 of FIG. 4 may configure and/or program the bandwidth-selectable filter 406 to operate and/or function (e.g., to filter) at the selected bandwidth(s) indicated by and/or corresponding to the bandwidth selection data 412 of FIG. 4. Following block 1004, control of the method 1000 of FIG. 10 proceeds to block 1006.

At block 1006, the acoustic emission sensor generates an acoustic emission signal (block 1006). For example, the acoustic emission sensor 402 of FIG. 4 may generate the acoustic emission signal 410 of FIG. 4 in response to one or more acoustic emission(s) (e.g., transient elastic waves) sensed, measured and/or detected via a sensing element of the acoustic emission sensor 402. Following block 1006, control of the example method 1000 of FIG. 10 proceeds to block 1008.

At block 1008, the configured bandwidth-selectable filter filters the acoustic emission signal to generate a filtered acoustic emission signal (block 1008). For example, the bandwidth-selectable filter 406 of FIG. 4 may filter the acoustic emission signal 410 of FIG. 4 according to the selected bandwidth(s) at which the bandwidth-selectable filter 406 was configured to operate and/or function in connection with block 1006, thereby generating a filtered acoustic emission signal. In some examples, the acoustic emission signal 410 may be amplified by a preamplifier (e.g., the preamplifier 404 of FIG. 4) prior to the bandwidth-selectable filter 406 filtering the acoustic emission signal 410 at block 1008. In other examples, the acoustic emission signal 410 may be amplified by a preamplifier (e.g., the preamplifier 404 of FIG. 6) after the bandwidth-selectable filter 406 has filtered the acoustic emission signal 410 at block 1008. Following block 1008, control of the example method 1000 of FIG. 10 proceeds to block 1010.

At block 1010, a data extractor of the acoustic emission sensor extracts time-averaged signal data (e.g., root mean square (RMS) data, average signal level (ASL) data, etc.) from the filtered acoustic emission signal (block 1010). For example, the data extractor 408 of the acoustic emission sensor 402 of FIG. 4 may extract and/or calculate root mean square data (e.g., a form of the time-averaged signal data 414 of FIG. 4) from the filtered acoustic emission signal. In some examples, the data extractor 408 may extract and/or calculate the root mean square data from the filtered acoustic emission signal by squaring the values of the filtered acoustic emission signal (e.g., squaring the function that defines the waveform of the filtered acoustic emission signal), by taking the average of the squared values (e.g., the average of the squared function), and by taking the square root of the average values (e.g., the square root of the average function). As another example, the data extractor 408 may additionally or alternatively extract and/or calculate average signal level data (e.g., another form of the time-averaged signal data 414) from the filtered acoustic emission signal by taking the average signal values (e.g., the average of the function that defines the waveform of the filtered acoustic emission signal) as a function of time. Following block 1010, control of the example method 1000 of FIG. 10 proceeds to block 1012.

At block 1012, the data extractor transmits the extracted time-averaged signal data from the acoustic emission sensor to an external data acquisition system (block 1012). For example, the data extractor 408 and/or, more generally, the acoustic emission sensor 402 of FIG. 4 may transmit the extracted time-averaged signal data 414 of FIG. 4 from the acoustic emission sensor 402 to an external data acquisition system. Thus, the data extractor 408 and/or, more generally, the acoustic emission sensor 402, transmits the time-averaged signal data 414 as filtered by the bandwidth-selectable filter 406 of the acoustic emission sensor 402 based on the selected bandwidth(s) corresponding to the bandwidth selection data 412 of FIG. 4. In some examples, the time-averaged signal data 414 may be the only data transmitted to the external data acquisition system by the data extractor 408 and/or the acoustic emission sensor 402. Following block 1012, the example method 1000 of FIG. 10 ends.

FIG. 11 is a flowchart representative of an example method 1100 for transmitting time-averaged signal data from the example external preamplifier device 702 of FIGS. 7-9. The example method 1100 of FIG. 11 begins with and/or otherwise includes receiving bandwidth selection data at the external preamplifier device indicating one or more selected bandwidth(s) for a bandwidth-selectable filter of the external preamplifier device (block 1102). For example, the bandwidth-selectable filter 706 and/or, more generally, the external preamplifier device 702 of FIG. 7 may receive the bandwidth selection data 712 of FIG. 7 indicating and/or corresponding to one or more selected bandwidth(s) for the bandwidth-selectable filter 706 of the external preamplifier device 702. In some examples, the bandwidth selection data may be received from an external data acquisition system. Following block 1102, control of the example method 1100 of FIG. 11 proceeds to block 1104.

At block 1104, the bandwidth-selectable filter is configured based on the bandwidth selection data (block 1104). For example, the bandwidth-selectable filter 706 and/or, more generally, the external preamplifier device 702 of FIG. 7 may configure and/or program the bandwidth-selectable filter 706 to operate and/or function (e.g., to filter) at the selected bandwidth(s) indicated by and/or corresponding to the bandwidth selection data 712 of FIG. 7. Following block 1104, control of the method 1100 of FIG. 11 proceeds to block 1106.

At block 1106, the external preamplifier device receives an acoustic emission signal generated by an acoustic emission signal (block 1106). For example, the external preamplifier device 702 of FIG. 7 may receive the acoustic emission signal 710 of FIG. 7 from an acoustic emission sensor. Following block 1106, control of the example method 1100 of FIG. 11 proceeds to block 1108.

At block 1108, the configured bandwidth-selectable filter filters the acoustic emission signal to generate a filtered acoustic emission signal (block 1108). For example, the bandwidth-selectable filter 706 of FIG. 7 may filter the acoustic emission signal 710 of FIG. 7 according to the selected bandwidth(s) at which the bandwidth-selectable filter 706 was configured to operate and/or function in connection with block 1106, thereby generating a filtered acoustic emission signal. In some examples, the acoustic emission signal 710 may be amplified by a preamplifier (e.g., the preamplifier 704 of FIG. 7) prior to the bandwidth-selectable filter 706 filtering the acoustic emission signal 710 at block 1108. In other examples, the acoustic emission signal 710 may be amplified by a preamplifier (e.g., the preamplifier 704 of FIG. 9) after the bandwidth-selectable filter 706 has filtered the acoustic emission signal 710 at block 1108. Following block 1108, control of the example method 1100 of FIG. 11 proceeds to block 1110.

At block 1110, a data extractor of the external preamplifier device extracts time-averaged signal data (e.g., root mean square (RMS) data, average signal level (ASL) data, etc.) from the filtered acoustic emission signal (block 1010). For example, the data extractor 708 of the external preamplifier device 702 of FIG. 7 may extract and/or calculate root mean square data (e.g., a form of the time-averaged signal data 714 of FIG. 7) from the filtered acoustic emission signal. In some examples, the data extractor 708 may extract and/or calculate the root mean square data from the filtered acoustic emission signal by squaring the values of the filtered acoustic emission signal (e.g., squaring the function that defines the waveform of the filtered acoustic emission signal), by taking the average of the squared values (e.g., the average of the squared function), and by taking the square root of the average values (e.g., the square root of the average function). As another example, the data extractor 708 may additionally or alternatively extract and/or calculate average signal level data (e.g., another form of the time-averaged signal data 714) from the filtered acoustic emission signal by taking the average signal values (e.g., the average of the function that defines the waveform of the filtered acoustic emission signal) as a function of time. Following block 1110, control of the example method 1100 of FIG. 11 proceeds to block 1112.

At block 1112, the data extractor transmits the extracted time-averaged signal data from the external preamplifier device to an external data acquisition system (block 1112). For example, the data extractor 708 and/or, more generally, the external preamplifier device 702 of FIG. 7 may transmit the extracted time-averaged signal data 714 of FIG. 7 from the external preamplifier device 702 to an external data acquisition system. Thus, the data extractor 708 and/or, more generally, the external preamplifier device 702, transmits the time-averaged signal data 714 as filtered by the bandwidth-selectable filter 706 of the external preamplifier device 702 based on the selected bandwidth(s) corresponding to the bandwidth selection data 712 of FIG. 7. In some examples, the time-averaged signal data 714 may be the only data transmitted to the external data acquisition system by the data extractor 708 and/or the external preamplifier device 702. Following block 1112, the example method 1100 of FIG. 11 ends.

Figure 12:
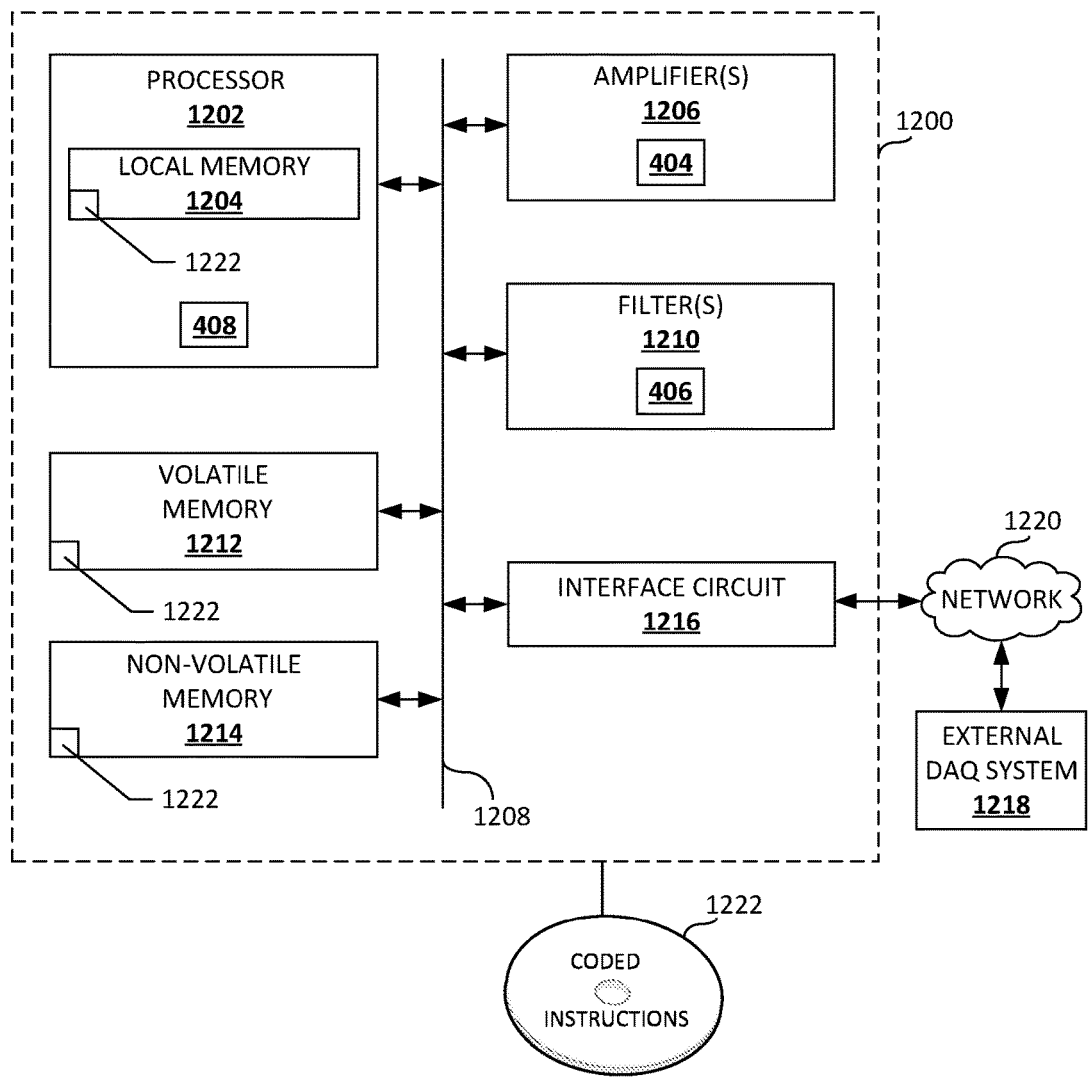
FIG. 12 is a block diagram of an example processor platform capable of executing instructions to implement the example method of FIG. 10 and the example acoustic emission sensor of FIGS. 4-6.

FIG. 12 is a block diagram of an example processor platform 1200 capable of executing instructions to implement the example method 1000 of FIG. 10 and the example acoustic emission sensor 402 of FIGS. 4-6. The processor platform 1200 of the illustrated example includes a processor 1202. The processor 1202 of the illustrated example is hardware. For example, the processor 1202 can be implemented by one or more integrated circuit(s), logic circuit(s), microprocessor(s) or controller(s) from any desired family or manufacturer. In the example of FIG. 12, the processor 1202 implements the example data extractor 408 of FIGS. 4-6. The processor 1202 of the illustrated example also includes a local memory 1204 (e.g., a cache).

The processor 1202 of the illustrated example is in communication with one or more example amplifier(s) 1206 via a bus 1208. In the example of FIG. 12, the amplifier(s) 1206 include the example preamplifier 404 of FIGS. 4-6. The processor 1202 of the illustrated example is also in communication with one or more example filter(s) 1210 via the bus 1208. In the example of FIG. 12, the filter(s) 1210 include the example bandwidth-selectable filter 406 of FIGS. 4-6.

The processor 1202 of the illustrated example is also in communication with a main memory including a volatile memory 1212 and a non-volatile memory 1214 via the bus 1208. The volatile memory 1212 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1214 may be implemented by flash memory and/or any other desired type of memory device. Access to the volatile memory 1212 and the non-volatile memory 1214 is controlled by a memory controller.

The processor platform 1200 of the illustrated example also includes an interface circuit 1216. The interface circuit 1216 may be implemented by any type of interface standard, such as an Ethernet interface, a universal serial bus (USB), and/or a PCI express interface. The interface circuit 1216 of the illustrated example includes a communication device such as a transmitter, a receiver, a transceiver, a modem and/or network interface card to facilitate exchange of data with a data acquisition system 1218 via a network 1220. In some examples, the network 1220 may be facilitated via 4-20 milliamp wiring and/or via one or more communication protocol(s) including, for example, HART, Foundation Fieldbus, Transmission Control Protocol/Internet Protocol (TCP/IP), Profinet, Modbus and/or Ethernet.

Coded instructions 1222 for implementing the method 1000 of FIG. 10 may be stored in the local memory 1204, in the volatile memory 1212, in the non-volatile memory 1214, and/or on a removable tangible computer readable storage medium such as a CD or DVD.

Figure 13:
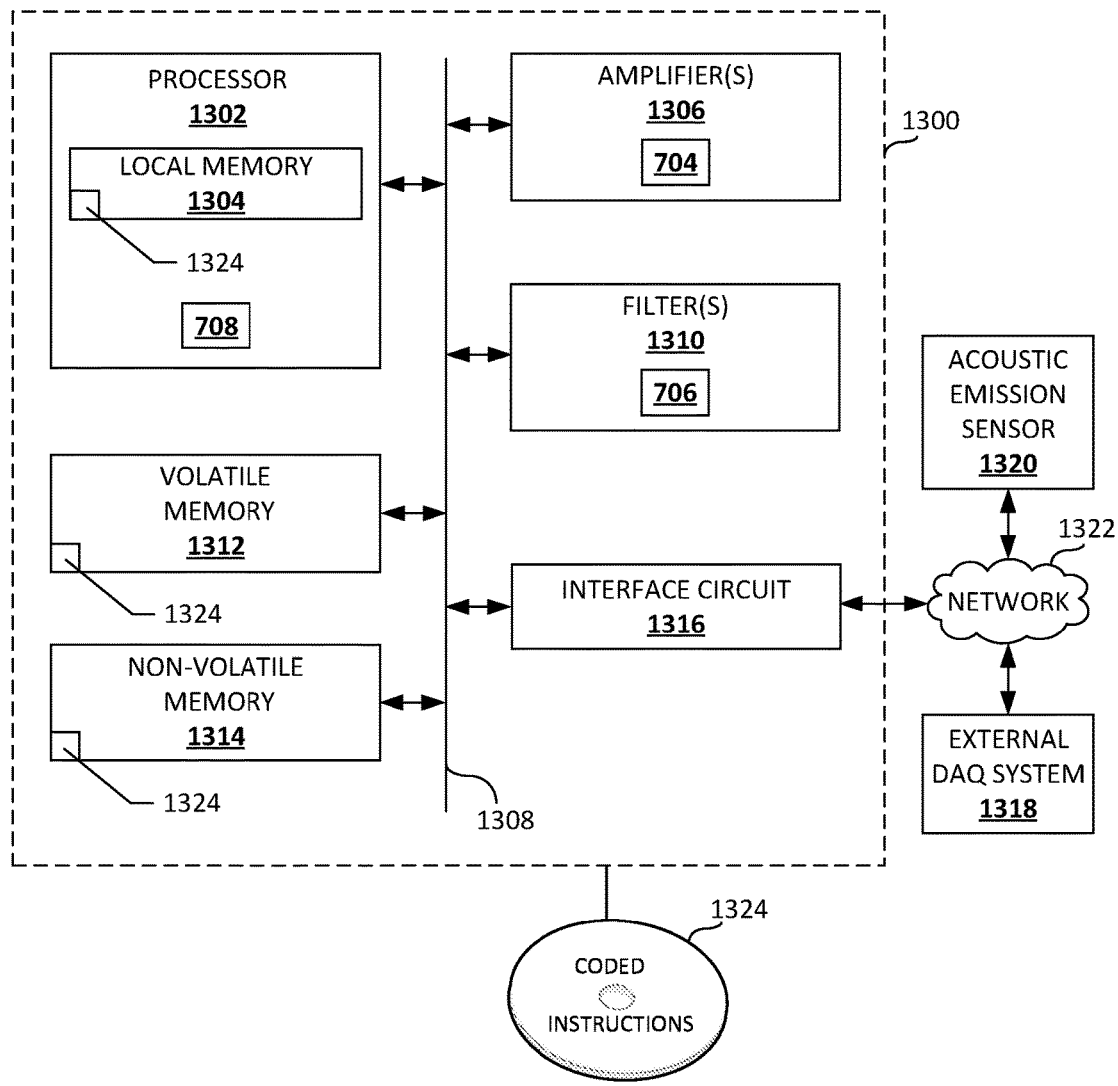
FIG. 13 is a block diagram of an example processor platform capable of executing instructions to implement the example method of FIG. 11 and the example external preamplifier device of FIGS. 7-9.

FIG. 13 is a block diagram of an example processor platform 1300 capable of executing instructions to implement the example method 1100 of FIG. 11 and the example external preamplifier device 702 of FIGS. 7-9. The processor platform 1300 of the illustrated example includes a processor 1302. The processor 1302 of the illustrated example is hardware. For example, the processor 1302 can be implemented by one or more integrated circuit(s), logic circuit(s), microprocessor(s) or controller(s) from any desired family or manufacturer. In the example of FIG. 13, the processor 1302 implements the example data extractor 708 of FIGS. 7-9. The processor 1302 of the illustrated example also includes a local memory 1304 (e.g., a cache).

The processor 1302 of the illustrated example is in communication with one or more example amplifier(s) 1306 via a bus 1308. In the example of FIG. 13, the amplifier(s)

1306 include the example preamplifier 704 of FIGS. 7-9. The processor 1302 of the illustrated example is also in communication with one or more example filter(s) 1310 via the bus 1308. In the example of FIG. 13, the filter(s) 1310 include the example bandwidth-selectable filter 706 of FIGS. 7-9.

The processor 1302 of the illustrated example is also in communication with a main memory including a volatile memory 1312 and a non-volatile memory 1314 via the bus 1308. The volatile memory 1312 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1314 may be implemented by flash memory and/or any other desired type of memory device. Access to the volatile memory 1312 and the non-volatile memory 1314 is controlled by a memory controller.

The processor platform 1300 of the illustrated example also includes an interface circuit 1316. The interface circuit 1316 may be implemented by any type of interface standard, such as an Ethernet interface, a universal serial bus (USB), and/or a PCI express interface. The interface circuit 1316 of the illustrated example includes a communication device such as a transmitter, a receiver, a transceiver, a modem and/or network interface card to facilitate exchange of data with a data acquisition system 1318 and/or an acoustic emission sensor 1320 via a network 1322. In some examples, the network 1322 may be facilitated via 4-20 milliamp wiring and/or via one or more communication protocol(s) including, for example, HART, Foundation Fieldbus, TCP/IP, Profinet, Modbus and/or Ethernet.

Coded instructions 1324 for implementing the method 1100 of FIG. 11 may be stored in the local memory 1304, in the volatile memory 1312, in the non-volatile memory 1314, and/or on a removable tangible computer readable storage medium such as a CD or DVD.

From the foregoing, it will be appreciated that the disclosed bandwidth-selectable acoustic emission apparatus and methods include a bandwidth-selectable filter (e.g., a software-programmable analog filter). In some disclosed examples, the bandwidth-selectable filter is integrated within an acoustic emission sensor. In other examples, the bandwidth-selectable filter is integrated within an external preamplifier device operatively located and/or positioned between an acoustic emission sensor and a data acquisition device.

Implementing the bandwidth-selectable filter via the disclosed bandwidth-selectable acoustic emission apparatus and methods advantageously enables the frequency content of an acoustic emission signal generated by an acoustic emission sensor to be resolved without the need for high speed sampling (e.g., without the need for a high end and costly data acquisition device). For example, an acoustic emission sensor or an external preamplifier device implementing the bandwidth-selectable filter may extract time-averaged signal data (e.g., root mean square (RMS) data, average signal level (ASL) data, etc.) from an acoustic emission signal filtered by the bandwidth-selectable filter, where the bandwidth-selectable filter is programmed and/or configured to filter the acoustic emission signal at one or more desired bandwidth(s)). The extracted time-averaged signal data, which has a lower frequency relative to the frequency of the acoustic emission signal itself, may then be transmitted from the acoustic emission sensor or the external preamplifier device to an external data acquisition device and/or an external data processing device without the need for high speed sampling.

In some disclosed examples, an apparatus comprises an acoustic emission sensor including a bandwidth-selectable filter and a data extractor. In some disclosed examples, the acoustic emission sensor is to generate an acoustic emission signal. In some disclosed examples, the bandwidth-selectable filter is to filter the acoustic emission signal based on a selected bandwidth to generate a filtered acoustic emission signal. In some disclosed examples, the data extractor is to extract time-averaged signal data from the filtered acoustic emission signal. In some disclosed examples, the data extractor is also to transmit the time-averaged signal data from the acoustic emission sensor to an external data acquisition system.

In some disclosed examples of the apparatus, the acoustic emission sensor further includes a preamplifier. In some disclosed examples, the bandwidth-selectable filter is integrated within the preamplifier. In some disclosed examples of the apparatus, the acoustic emission sensor further includes a preamplifier to amplify the acoustic emission signal prior to the bandwidth-selectable filter filtering the acoustic emission signal. In some disclosed examples of the apparatus, the acoustic emission sensor further includes a preamplifier to amplify the filtered acoustic emission signal.

In some disclosed examples of the apparatus, the selected bandwidth is based on bandwidth selection data to be received at the acoustic emission sensor from the external data acquisition system. In some disclosed examples, the external data acquisition system includes a data acquisition device and a data processing device.

In some disclosed examples of the apparatus, the time-averaged signal data includes root mean square data. In some disclosed examples of the apparatus, the time-averaged signal data includes average signal level data.

In some disclosed examples, a method comprises filtering an acoustic emission signal based on a selected bandwidth of a bandwidth-selectable filter of an acoustic emission sensor to generate a filtered acoustic emission signal. In some disclosed examples, the acoustic emission signal is generated via the acoustic emission sensor. In some disclosed examples, the method further comprises extracting time-averaged signal data from the filtered acoustic emission signal. In some disclosed examples, the method further comprises transmitting the time-averaged signal data from the acoustic emission sensor to an external data acquisition system.

In some disclosed examples of the method, the acoustic emission sensor further includes a preamplifier. In some disclosed examples, the bandwidth-selectable filter is integrated within the preamplifier. In some disclosed examples of the method, the acoustic emission sensor further includes a preamplifier to amplify the acoustic emission signal prior to the filtering of the acoustic emission signal. In some disclosed examples of the method, the acoustic emission sensor further includes a preamplifier to amplify the filtered acoustic emission signal.

In some disclosed examples of the method, the selected bandwidth is based on bandwidth selection data received at the acoustic emission sensor from the external data acquisition system. In some disclosed examples, the external data acquisition system includes a data acquisition device and a data processing device.

In some disclosed examples of the method, the time-averaged signal data includes root mean square data. In some disclosed examples of the method, the time-averaged signal data includes average signal level data.

In some disclosed examples, an apparatus comprises an external preamplifier device including a bandwidth-selectable filter and a data extractor. In some disclosed examples, the external preamplifier device is to receive an acoustic emission signal from an acoustic emission sensor. In some disclosed examples, the bandwidth-selectable filter is to filter the acoustic emission signal based on a selected bandwidth to generate a filtered acoustic emission signal. In some disclosed examples, the data extractor is to extract time-averaged signal data from the filtered acoustic emission signal. In some disclosed examples, the data extractor is also to transmit the time-averaged signal data from the external preamplifier device to an external data acquisition system.

In some disclosed examples of the apparatus, the external preamplifier device further includes a preamplifier. In some disclosed examples, the bandwidth-selectable filter is integrated within the preamplifier. In some disclosed examples of the apparatus, the external preamplifier device further includes a preamplifier to amplify the acoustic emission signal prior to the bandwidth-selectable filter filtering the acoustic emission signal. In some disclosed examples of the apparatus, the external preamplifier device further includes a preamplifier to amplify the filtered acoustic emission signal.

In some disclosed examples of the apparatus, the selected bandwidth is based on bandwidth selection data to be received at the external preamplifier device from the external data acquisition system. In some disclosed examples, the data acquisition system includes a data acquisition device and a data processing device.

In some disclosed examples of the apparatus, the time-averaged signal data includes root mean square data. In some disclosed examples of the apparatus, the time-averaged signal data includes average signal level data.

In some disclosed examples, a method comprises filtering an acoustic emission signal based on a selected bandwidth of a bandwidth-selectable filter of an external preamplifier device to generate a filtered acoustic emission signal. In some disclosed examples, the acoustic emission signal is received at the external preamplifier device from an acoustic emission sensor. In some disclosed examples, the method further comprises extracting time-averaged signal data from the filtered acoustic emission signal. In some disclosed examples, the method further comprises transmitting the time-averaged signal data from the external preamplifier device to an external data acquisition system.

In some disclosed examples of the method, the external preamplifier device further includes a preamplifier. In some disclosed examples, the bandwidth-selectable filter is integrated within the preamplifier. In some disclosed examples of the method, the external preamplifier device further includes a preamplifier to amplify the acoustic emission signal prior to the filtering of the acoustic emission signal. In some disclosed examples of the method, the external preamplifier device further includes a preamplifier to amplify the filtered acoustic emission signal.

In some disclosed examples of the method, the selected bandwidth is based on bandwidth selection data received at the external preamplifier device from the external data acquisition system. In some disclosed examples, the external data acquisition system includes a data acquisition device and a data processing device.

In some disclosed examples of the method, the time-averaged signal data includes root mean square data. In some disclosed examples of the method, the time-averaged signal data includes average signal level data.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. An apparatus, comprising:
an integrated acoustic emission sensor including a bandwidth-selectable analog filter and a data extractor, the integrated acoustic emission sensor to generate an analog acoustic emission signal, the bandwidth-selectable analog filter to filter the analog acoustic emission signal based on a software-programmed bandwidth to generate a filtered analog acoustic emission signal, the data extractor to extract a time-averaged analog signal from the filtered analog acoustic emission signal, the data extractor to transmit the time-averaged analog signal from the integrated acoustic emission sensor to an external data acquisition system.

2. The apparatus of claim 1, where the integrated acoustic emission sensor further includes a preamplifier, the bandwidth-selectable analog filter being integrated within the preamplifier.

3. The apparatus of claim 1, wherein the integrated acoustic emission sensor further includes a preamplifier to amplify the analog acoustic emission signal prior to the bandwidth-selectable analog filter filtering the analog acoustic emission signal.

4. The apparatus of claim 1, wherein the integrated acoustic emission sensor further includes a preamplifier to amplify the filtered analog acoustic emission signal.

5. The apparatus of claim 1, wherein the software-programmed bandwidth is based on bandwidth selection data to be received at the integrated acoustic emission sensor from the external data acquisition system.

6. The apparatus of claim 5, wherein the external data acquisition system includes a data acquisition device and a data processing device.

7. The apparatus of claim 1, wherein the time-averaged analog signal includes root mean square data.

8. The apparatus of claim 1, wherein the time-averaged analog signal includes average signal level data.

9. The apparatus of claim 1, wherein the analog acoustic emission signal has a frequency content, and wherein the bandwidth-selectable analog filter and the data extractor of the integrated acoustic emission sensor are configured to resolve a frequency component of the frequency content at the integrated acoustic emission sensor.

10. The apparatus of claim 1, wherein the data extractor is to transmit the time-averaged analog signal from the integrated acoustic emission sensor to the external data acquisition system via 4-20 milliamp wiring.

11. The apparatus of claim 1, wherein the integrated acoustic emission sensor does not include an analog to digital converter.

12. A method, comprising:
filtering an analog acoustic emission signal at an integrated acoustic emission sensor based on a software-programmed bandwidth of a bandwidth-selectable analog filter of the integrated acoustic emission sensor to generate a filtered analog acoustic emission signal, the analog acoustic emission signal being generated via the integrated acoustic emission sensor;

extracting, at the integrated acoustic emission sensor, a time-averaged analog signal from the filtered analog acoustic emission signal; and transmitting the time-averaged analog signal from the integrated acoustic emission sensor to an external data acquisition system.

13. The method of claim 12, further comprising amplifying the analog acoustic emission signal or the filtered analog acoustic emission signal via a preamplifier of the integrated acoustic emission sensor, the bandwidth-selectable analog filter being integrated within the preamplifier.

14. The method of claim 12, further comprising amplifying the analog acoustic emission signal via a preamplifier of the integrated acoustic emission sensor prior to the filtering of the analog acoustic emission signal.

15. The method of claim 12, further comprising amplifying the filtered analog acoustic emission signal via a preamplifier of the integrated acoustic emission sensor.

16. The method of claim 12, further comprising receiving bandwidth selection data at the integrated acoustic emission sensor from the external data acquisition system, the software-programmed bandwidth being based on the bandwidth selection data.

17. The method of claim 12, wherein the time-averaged analog signal includes root mean square data.

18. The method of claim 12, wherein the time-averaged analog signal includes average signal level data.

19. The method of claim 12, wherein the analog acoustic emission signal has a frequency content, and wherein the filtering and the extracting resolve a frequency component of the frequency content at the integrated acoustic emission sensor.

20. The method of claim 12, wherein the time-averaged analog signal is transmitted from the integrated acoustic emission sensor to the external data acquisition system via 4-20 milliamp wiring.

* * * * *